US012465381B1

(12) United States Patent
Hakki

(10) Patent No.: US 12,465,381 B1
(45) Date of Patent: Nov. 11, 2025

(54) FENESTRATED BALLOON CATHETER SYSTEM

(71) Applicant: A-Hamid Hakki, Dunedin, FL (US)

(72) Inventor: A-Hamid Hakki, Dunedin, FL (US)

( * ) Notice: Subject to any disclaimer, the term of this patent is extended or adjusted under 35 U.S.C. 154(b) by 0 days.

(21) Appl. No.: 19/040,898

(22) Filed: Jan. 30, 2025

(51) Int. Cl.

| | |
|---|---|
| ***A61B 17/22*** | (2006.01) |
| ***A61B 17/00*** | (2006.01) |
| ***A61M 25/10*** | (2013.01) |

(52) U.S. Cl.
CPC ........ *A61B 17/22* (2013.01); *A61B 17/00234* (2013.01); *A61M 25/10* (2013.01); *A61B 2017/00238* (2013.01); *A61B 2017/00305* (2013.01); *A61B 2017/00544* (2013.01); *A61B 2017/00557* (2013.01); *A61B 2017/22038* (2013.01); *A61B 2017/22065* (2013.01); *A61M 2025/1086* (2013.01); *A61M 2025/1093* (2013.01); *A61M 2210/12* (2013.01)

(58) Field of Classification Search
CPC .. A61M 2025/1095; A61M 2025/1097; A61M 2025/1061; A61M 25/10; A61M 25/007; A61M 25/104
See application file for complete search history.

(56) References Cited

U.S. PATENT DOCUMENTS

2001/0031982 A1* 10/2001 Peterson .................. A61F 2/01 604/102.01
2002/0082592 A1* 6/2002 Lary ............. A61B 17/320725 606/15
2002/0193735 A1* 12/2002 Stiger ................ A61M 25/104 604/101.01
2018/0185192 A1* 7/2018 Mazzone .......... A61M 25/0043
2023/0130458 A1* 4/2023 Walzman ....... A61B 17/320758 606/41

* cited by examiner

*Primary Examiner* — Mohamed G Gabr
(74) *Attorney, Agent, or Firm* — Larson & Larson; Frank Liebenow

(57) ABSTRACT

A fenestrated balloon catheter includes a body having a proximal segment, a central segment, and a distal segment. The proximal segment has a first set of fenestrations, and the distal segment has a second set of fenestrations. An elongated tubular structure wraps around the proximal segment, the central segment, and the distal segment. After the fenestrated balloon catheter is inserted into a tube (e.g., a blood vessel), fluid pressure is inserted into the elongated tubular structure to expand the fenestrated balloon catheter, thereby touching the inner walls of the tube or expanding the inner walls of the tube. The first set and second set of fenestrations provide for flow of a fluid (e.g. blood) through the fenestrated balloon catheter after expansion.

16 Claims, 6 Drawing Sheets

FENESTRATED BALLOON CATHETER SYSTEM

FIELD OF THE INVENTION

This invention relates to the field of medicine, in particular, to surgical devices inserted into a patient's vascular system that, for example, deliver medications, ultrasound, laser, and/or pacemaker therapy directly to the tissues.

BACKGROUND OF THE INVENTION

Balloon catheters have been used for intravascular applications for many years to dilate blockages, perform ultrasound or laser lithotripsy, and to control vascular dissections. When the balloon catheters of the prior art are inflated, blood flow is interrupted and prolonged inflation may cause complications due to decreased blood flow resulting in tissue such as ischemia or necrosis. Previously, auto perfusion balloon catheters provided minimal blood flow through a central lumen and multiple side holes in the proximal and distal shafts but have not been very effective and are no longer in clinical use. On Jan. 16, 1964 Dotter and Judkins performed the first balloon angioplasty of a lower extremity. On Sep. 16, 1977, Andreas Gruntzig performed the first balloon coronary angioplasty. Such balloon technology often blocked blood flow for blood through the blood vessel in which they are inserted.

What is needed is a mechanism that provides balloon inflation that is needed for a specific purpose such as angioplasty, valvuloplasty, transcatheter aortic valve replacement (TAVR), aortic dissection, occluded vessel, coronary stenosis, vascular lithotripsy or laser therapy without compromising blood flow.

SUMMARY OF THE INVENTION

In one embodiment, a fenestrated balloon catheter is disclosed including a body having a proximal segment, a central segment, and a distal segment. The proximal segment has a first set of fenestrations, and the distal segment has a second set of fenestrations. An elongated tubular structure wraps around the proximal segment, the central segment, and the distal segment.

In another embodiment, a system for delivering therapy within a body-tube is disclosed, including a fenestrated balloon catheter that includes a body having a proximal segment, a central segment, and a distal segment. The proximal segment has a first set of fenestrations, and the distal segment has a second set of fenestrations. An elongated tubular structure wraps around the proximal segment, the central segment, and the distal segment. There is an internal conduit for accepting a guide wire. The guide wire is positioned in the body-tube and an end of the guide wire is threaded through the internal conduit of the fenestrated balloon catheter such that the fenestrated balloon catheter is guided into the body-tube by the guide wire. The fenestrated balloon catheter is pushed through the body-tube until the fenestrated balloon catheter reaches a location for delivering the therapy and then, fluid pressure is injected into the elongated tubular structure, thereby the fenestrated balloon catheter expands within the body-tube such that the fenestrated balloon catheter either touches inner walls of the tube or expands to stretch the body-tube.

In another embodiment, a method for delivering therapy within a body-tube is disclosed. The method includes positioning a guide wire in the body-tube (e.g., a blood vessel) and threading an end of the guide wire through an internal conduit of a fenestrated balloon catheter. The fenestrated balloon catheter has a body with a proximal segment, a central segment, and a distal segment. The proximal segment has a first set of fenestrations, and the distal segment has a second set of fenestrations. An elongated tubular structure wraps around the proximal segment, the central segment, and the distal segment. The method continues with pushing the fenestrated balloon catheter through the body-tube until the fenestrated balloon catheter reaches a location for delivering the therapy and then providing fluid pressure into the elongated tubular structure, thereby expanding the fenestrated balloon catheter within the body-tube such that the fenestrated balloon catheter either touches inner walls of the body-tube or expands to stretch the body-tube.

In some embodiments, the fenestrated balloon catheter system is directed to surgical devices inserted into a patient's vascular system for delivering medications, ultrasound, laser, and pacemaker therapy directly to the tissues.

In some embodiments, the fenestrated balloon catheter system is directed to balloon catheter systems which are inserted into a patient's vascular system and remain in a relatively fixed location during or subsequent to a medical procedure.

In some embodiments, the fenestrated balloon catheter system is directed to a balloon catheter system which includes a balloon construction which allows for retention and simultaneous application of therapeutic interventions while maintaining blood flow proximal and distal to the balloon.

In some embodiments, the fenestrated balloon catheter system is directed to a balloon catheter system which includes at one or more conduits attached to the balloon's inner (or outer) surface that is/are filled with liquid under pressure to cause deployment (expansion) of the balloon walls against the inner lining of the vascular system or valvular structures.

In some embodiments, the fenestrated balloon catheter system is directed to a balloon catheter system having a one or more balloon orifices formed through the proximal as well as distal segments of the balloon.

In some embodiments, the fenestrated balloon catheter system is directed to a balloon catheter system which has a mechanism for providing medicants to be inserted through the conduits attached to the balloon for treating a particular ailment.

In some embodiments, the fenestrated balloon catheter system is directed to an open balloon catheter system which is inserted into the vascular system of a patient for restraining the balloon catheter from movement while simultaneously providing therapeutic interventions with ultrasound, laser, pacemaker therapy and medications.

In some embodiments, the fenestrated balloon catheter system is directed to a balloon catheter is placed in a diseased heart valve such as aortic stenosis to expand the aortic valve orifice without disrupting blood flow through the valve by way of fenestration in the proximal and distal parts of the balloon.

In some embodiments, the fenestrated balloon catheter system is directed to a balloon that is placed at the site of vascular tear or dissection, such as the aorta to stop bleeding while maintaining blood flow to the distal aorta and downstream tissues.

In some embodiments, during a cardiac valve replacement such as TAVR (transcatheter aortic valve replacement), the fenestrated balloon catheter is placed distal to the aortic valve to capture debris or clots that result from manipulations of the diseased heart valve.

In some embodiments, the fenestrated balloon catheter is placed to disrupt vascular plaque (angioplasty) and improve blood flow through the diseased coronary artery.

In some embodiments, the fenestrated balloon catheter provides pacing cardiac tissue in the event of profound bradycardia or heart blockage.

In some embodiments, the fenestrated balloon catheter provides for smaller orifice dimensions in the proximal balloon segment to capture unwanted blood clots, plaque and other debris entering the balloon segment from the larger orifices of the distal segment, while maintaining blood flow.

In some embodiments, the fenestrated balloon catheter provides for larger orifice dimensions in the proximal balloon segment to capture unwanted blood clots, plaque and other debris from exiting the balloon segment from the smaller orifices of the distal segment, while maintaining blood flow.

BRIEF DESCRIPTION OF DRAWINGS

The invention can be best understood by those having ordinary skill in the art by reference to the following detailed description when considered in conjunction with the accompanying drawings in which.

DETAILED DESCRIPTION OF THE INVENTION

Figure 1:
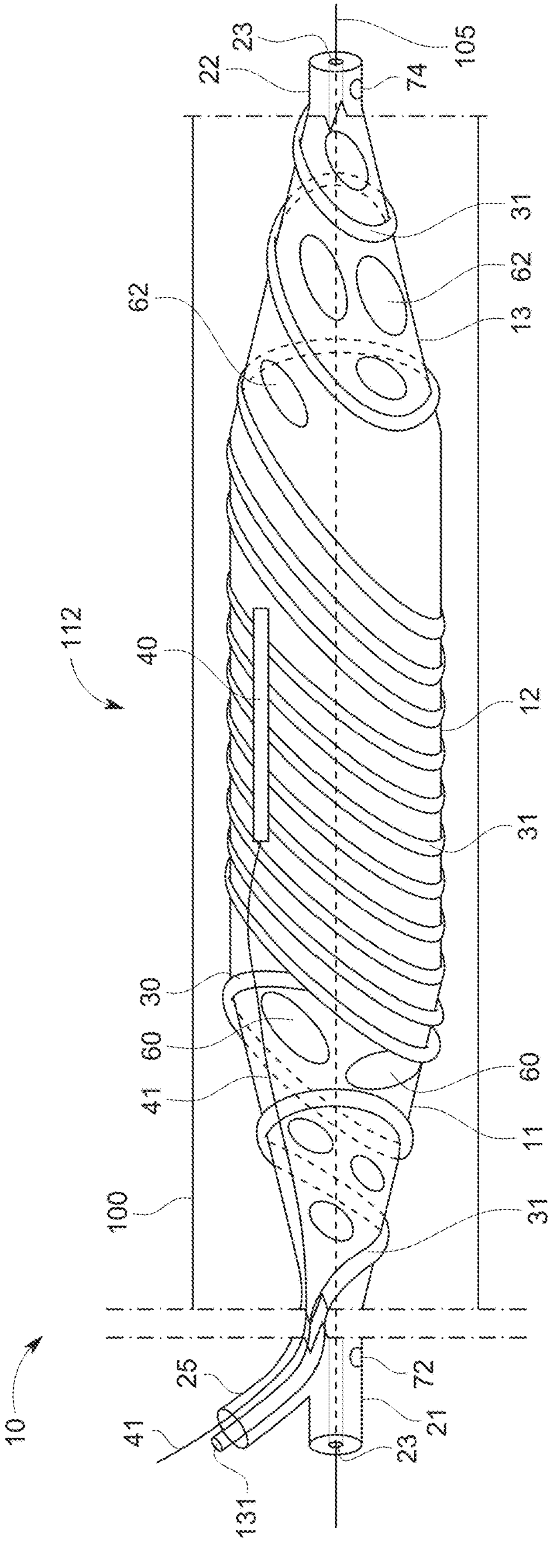
FIG. 1 is a is a schematic view of the fenestrated balloon catheter system shown in a partially deflated configuration with a tube structure affixed/integrated in the body of the fenestrated balloon catheter and having an optional, longitudinally placed, ultrasound emitter.

Reference will now be made in detail to the presently preferred embodiments of the invention, examples of which are illustrated in the accompanying drawings. Throughout the following detailed description, the same reference numerals refer to the same elements in all figures.

Throughout this description, the term "balloon" or "fenestrated balloon" refer to a device that is positioned in a body-tube, for example using a catheter, and inflated to expand within the body-tube for any known reason such as holding the fenestrated balloon in place or increasing the diameter of the body-tube. Such tube is often a blood vessel (artery, vein, capillary, though any body-tube is anticipated (e.g., lymph ducts, bile ducts, airway tubes, gastric tubes). The fenestrated balloon has features that allow a fluid (e.g., blood, air, urine) to flow through such that the fenestrated balloon does not significantly block such flow. In some embodiments, the fenestrated balloon provides medications directly to an area of the body-tube in which it is placed (e.g., chemotherapy). In some embodiments, the fenestrated balloon carries other medical devices such as ultrasonic emitters (e.g., for removing calcified coronary plaques or dissolving kidney stones), lasers, etc.

The fenestrated balloon catheter 10 includes an elongated tubular structure 31/31A/31B/31C (see FIGS. 4, 5 and 6) that is affixed to or integrated into the inside and/or the outside of the wall 12 of the fenestrated balloon catheter 10 (e.g., using an adhesive of a biologically compatible material or integrated fabrication technique). When the elongated tubular structure 31/31A/31B/31C is pressurized with a fluid from an input port 131/33, the elongated tubular structure 31/31A/31B/31C expands, having a cross-sectional shape that, in some embodiments, is circular, oval, square or rectangular. When the elongated tubular structure 31/31A is not pressurized, the elongated tubular structure 31/31A/31B/31C relaxes allowing passing of the fenestrated balloon catheter 10 through a body-tube 100 (see FIGS. 1-3) such as a blood vessel. It is fully anticipated that the body-tube 100 be a tube such as a blood vessel, duct (e.g. bile duct), air passage, or any tube of an animal such as a human being.

Figure 4:
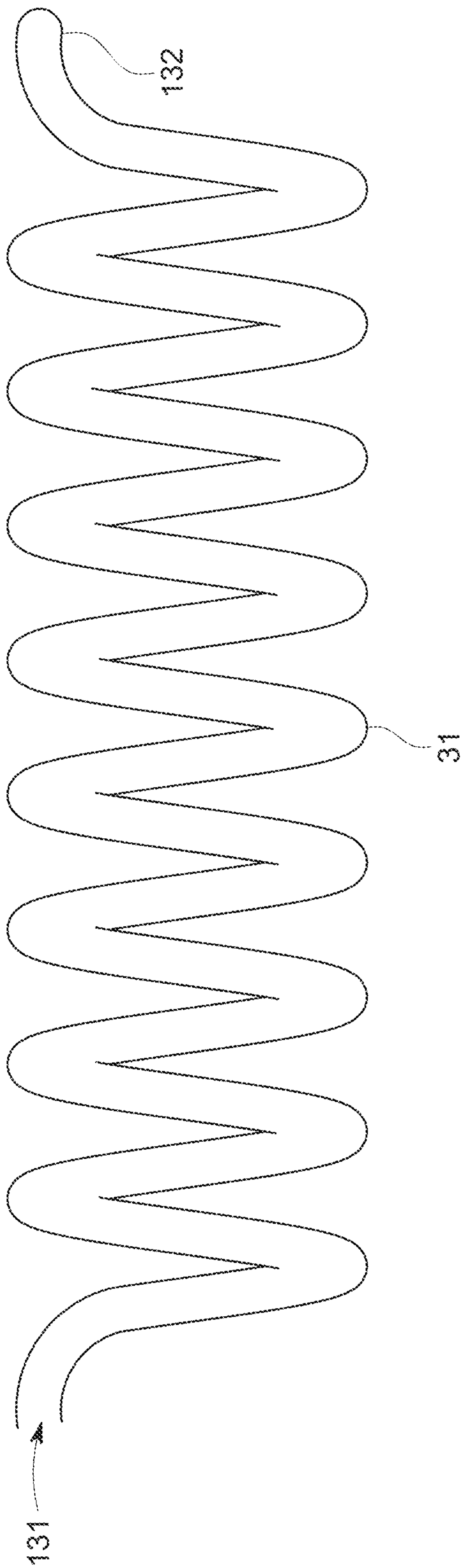
FIG. 4 is a is a schematic view of one embodiment of the elongated tube structure of the fenestrated balloon catheter system.
Figure 5:
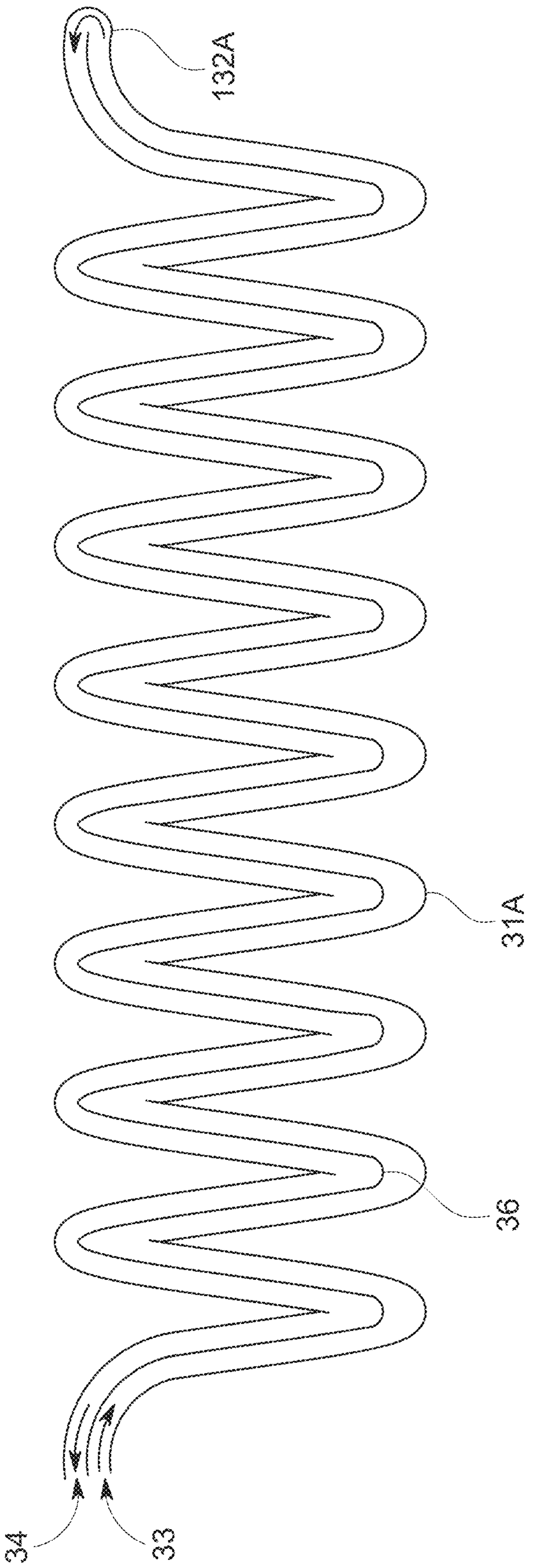
FIG. 5 is a is a schematic view of one embodiment of the elongated tube structure of the fenestrated balloon catheter system.
Figure 6:
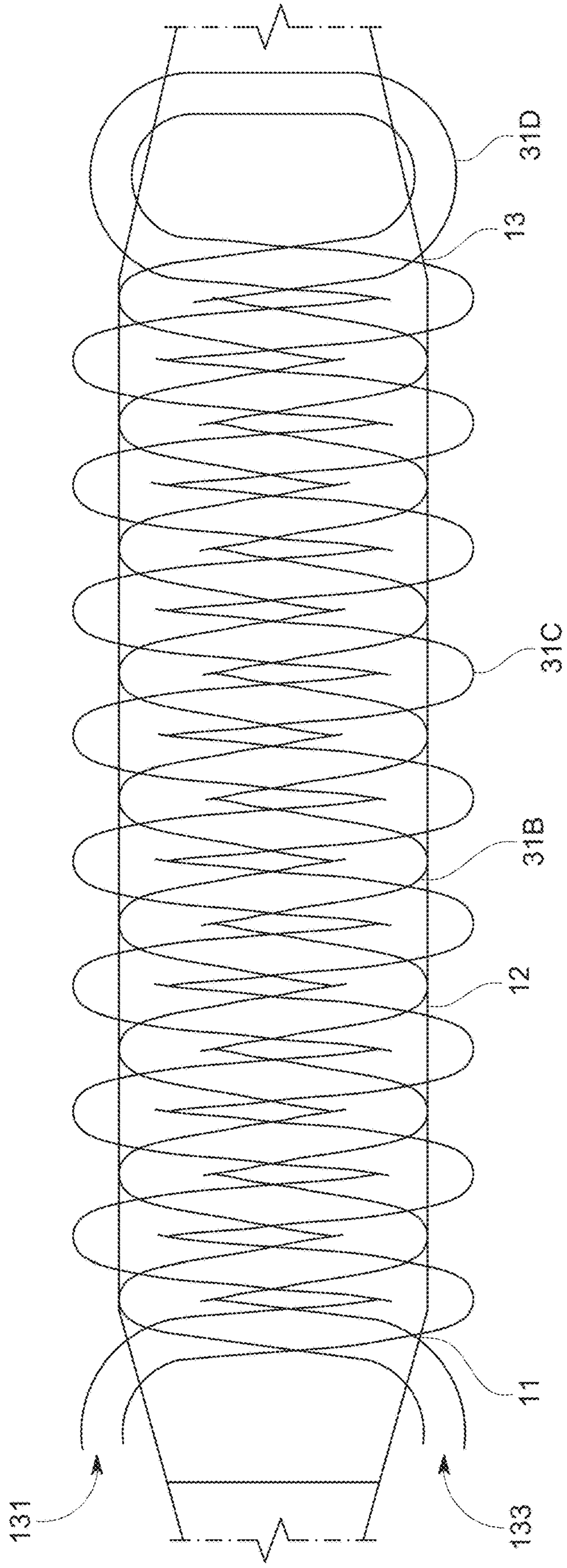
FIG. 6 is a is a schematic view of one embodiment of the elongated tube structure of the fenestrated balloon catheter system.

Note that in FIGS. 4, 5, and 6, the elongated tubular structure 31/31A/31B/31C is shown in a pressurize configuration as, when not pressurized, it is anticipated that the elongated tubular structure 31/31A/31B/31C be collapsed and, in some embodiments, relatively flat.

In some embodiments, the elongated tubular structure 31/31A/31B/31C is made from a biologically compatible material that is a flexible, non-expanding plastic or similar. In some embodiments, the elongated tubular structure 31 is sealed at an end 132 that is distal from the input port 131 (see FIG. 4). In some embodiments, the elongated tubular structure 31/31A/31B/31C spirals around the wall 12 of the fenestrated balloon catheter 10 so that, when pressurized, the elongated tubular structure 31/31A/31B/31C expands the wall 12 of the fenestrated balloon catheter 10.

In some embodiments, the elongated tubular structure 31/31A/31B/31C is a simple tube 31 as shown in FIG. 4 having an input port 131 at one end and sealed at an end 132 that is distal from the input port 131.

In some embodiments as shown in FIG. 5, the elongated tubular structure 31A is divided by a partition 36 along the entire length except at the sealed end 132A, having an input port 33 and an output port 34 at one end and looping back at the sealed end 132A. In this embodiment, a fluid is inputted into the input port 33 of the conduit 31A under pressure and the fluid flows through one side of the elongated tubular structure 31A, changing direction at the sealed end 132A of the elongated tubular structure 31A to flow back through a second side of the elongated tubular structure 31A and out the outlet output port 34. The level of the pressure is controlled by a differential pressure between the input port 33 and the output port 34. This embodiment provides for a flow-thru of the fluid for providing various therapeutic properties such as heating or cooling.

In some embodiments as shown in FIG. 6, the elongated tubular structure 31/31A/31B/31C is a dual set of elongated tubes 31B/31C, having an input port 131 and an output port 133 at one end and connected to each other (or a single elongated tube as shown) at the distal end 31D. In this embodiment, a fluid is inputted into the input port 131 under pressure and the fluid flows through the first elongated tube 31B, changing direction at the distal end 31D of the elongated tube 31B to flow back through the second elongated tube 31C and out the outlet output port 133. The level of the pressure is controlled by a differential pressure between the input port 131 and the output port 133. This embodiment provides for a flow-thru of the fluid for providing various therapeutic properties such as heating or cooling. Further, in some embodiments, one of the first elongated tube 31B and the second elongated tube 31C are formed/affixed on/to an outside surface of the proximal segment 11, the wall 12, and the distal segment 13 while the other of the first elongated tube 31B and the second elongated tube 31C are formed/affixed on/to an inside surface of the proximal segment 11, the wall 12, and the distal segment 13. As shown in FIG. 6, the first elongated tube 31B ais formed/affixed on/to the inside surface of the proximal segment 11, the wall 12, and the distal segment 13 and the second elongated tube 31C ais formed/affixed on/to the outside surface of the proximal segment 11, the wall 12, and the distal segment 13.

In absence of pressure within the elongated tubular structure 31/31A/31B/31C, the elongated tubular structure 31/31A/31B/31C collapses causing deflation of the fenestrated balloon catheter 10. In some embodiments, the fluid contains therapeutic agents delivered in close proximity to the lining of the body-tube 100 in which the fenestrated balloon catheter 10 is inserted. In some embodiments, the fluid is heated/cooled to provide a desired temperature to the surface of the fenestrated balloon catheter 10, thereby heating or cooling the lining of the body-tube 100 in which the fenestrated balloon catheter 10 is inserted. This is often the case when performing procedures in arteries such as for stenting or ultrasound lithotripsy. In such, when concerned with particulate matter (e.g., blood clots), the smaller fenestrations 60A are at the proximal end to capture the particulate matter within the fenestrated balloon catheter 10.

Figure 3:
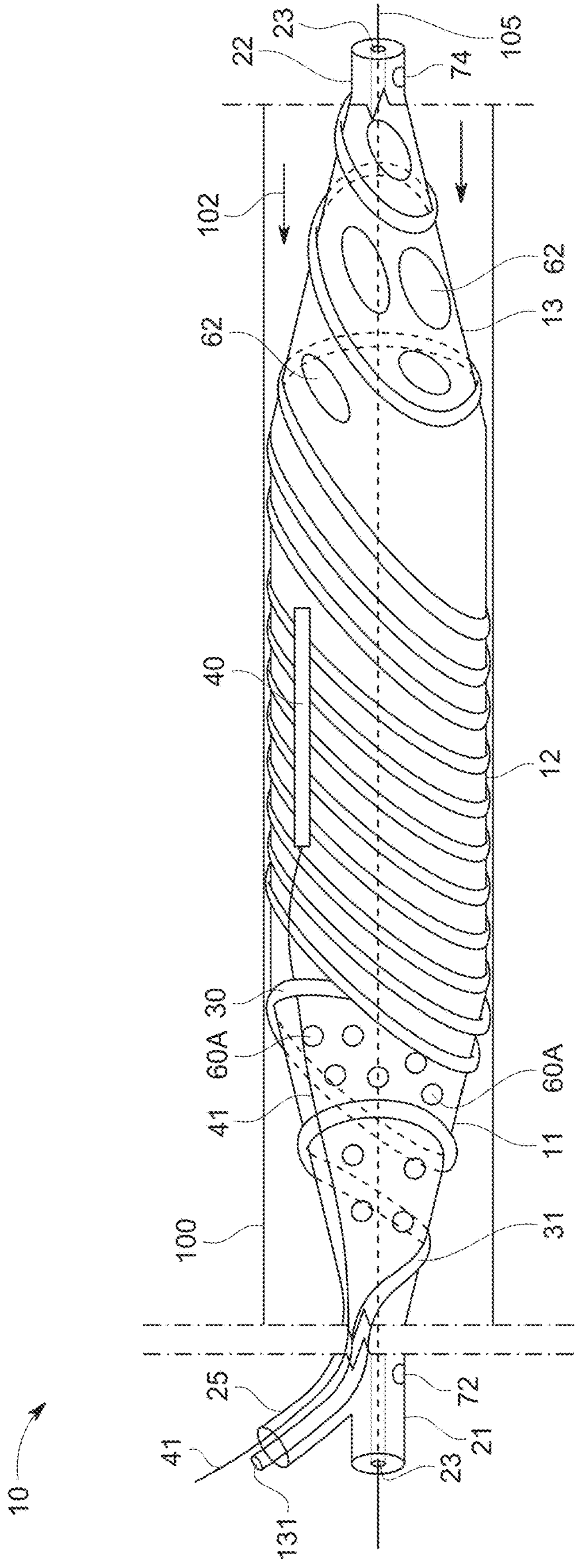
FIG. 3 is a is a second schematic view of the fenestrated balloon catheter system shown in an inflated configuration with a tube structure affixed/integrated in the body of the fenestrated balloon catheter and having an optional, longitudinally placed, ultrasound emitter.

Note that, as the fenestrated balloon catheter 10 is typically inserted through an access into a body-tube 100, the distal end of the fenestrated balloon catheter 10 is that which is inserted first (e.g., furthest from the access) and the proximal end is that which is closest to the access. In some usage scenarios, body fluid (e.g., blood, air) flows from the distal end towards the proximal end such that as the fenestrated balloon catheter 10 is being inserted, it is inserted against the flow of the body fluid (e.g., as shown in FIG. 3). In a fenestrated balloon catheter 10 that captures particulate material within the fenestrated balloon catheter 10 (see FIG. 3) the larger fenestrations 60 are positioned to receive the body fluid flow (e.g., distal/proximal) and the smaller fenestrations 60A are positioned away from the flow of body fluid to capture the particulate matter (e.g., proximal/distal).

Referring to FIG. 1, the fenestrated balloon catheter 10 is shown. The fenestrated balloon catheter 10 is shown in a partially deflated configuration and has been inserted into a body-tube 100 (e.g., a blood vessel of a patient). Note that a fully deflated configuration (fully deflated has the proximal segment, central segment, and distal segment around the body 21 and 22) is not shown for brevity and clarity reasons). The fenestrated balloon catheter 10 typically traverses the body-tube in the fully deflated mode.

Three sections of the fenestrated balloon catheter 10 include a proximal segment 11, a central segment 112 and a distal segment 13. In some embodiments, the proximal segment 11 and distal segment 13 are generally cone shaped though other shapes are fully anticipated, and the central segment is generally cylindrical. Fenestrations 60/62 or openings in the proximal segment 11 and distal segment 13 allow fluids within the body-tube 100 (e.g., blood, urine, air, bile) to flow through the proximal segment 11, central segment 12, and distal segment 13, especially while the fenestrated balloon catheter 10 is inflated as shown in FIGS. 2 and 3.

Figure 2:
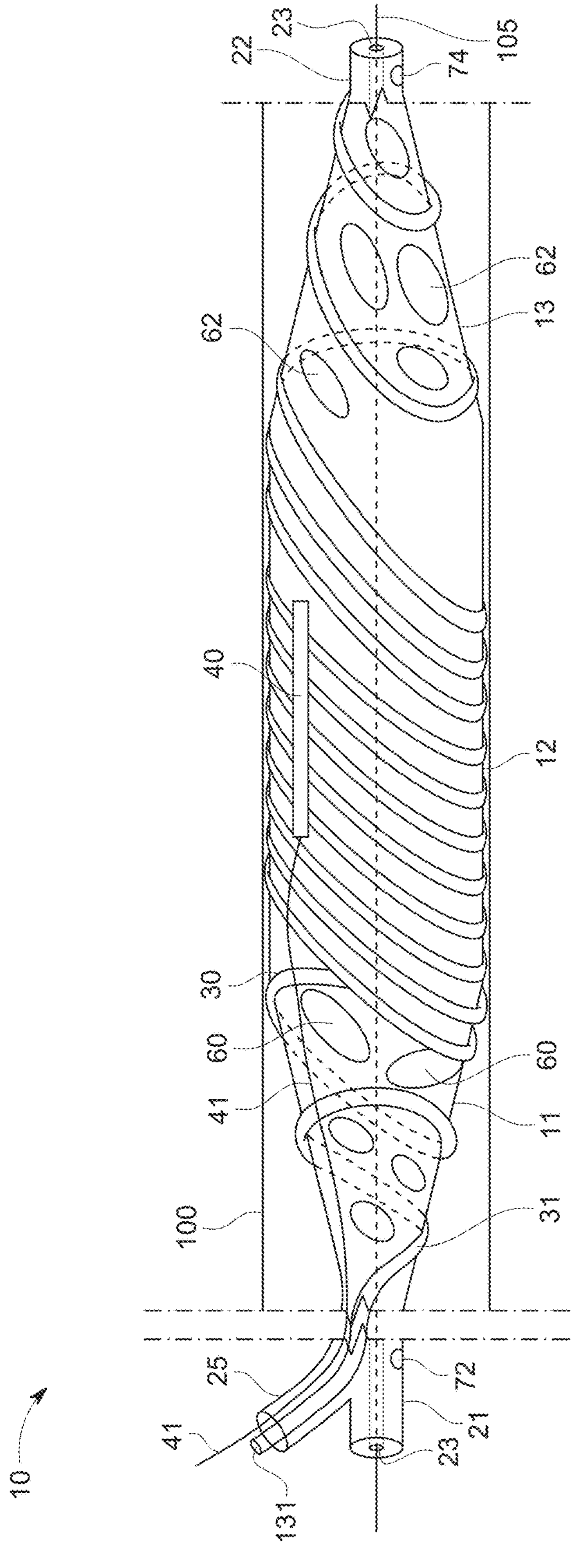
FIG. 2 is a is a schematic view of the fenestrated balloon catheter system shown in an inflated configuration with a tube structure affixed/integrated in the body of the fenestrated balloon catheter and having an optional, longitudinally placed, ultrasound emitter.

Note that, for brevity and clarity reasons, the fenestrated balloon catheter 10 shown in FIGS. 1, 2, and 3 include the elongated tubular structure 31 as shown in FIG. 4, though it is fully anticipated that other elongated tubular structures be used such as the elongated tubular structure 31A shown in FIG. 5 or the elongated tube structure 31B/31C shown in FIG. 6.

In some embodiments, the elongated tubular structure 31/31A/31B/31C is helically interfaced to the inside or outside of the proximal segment 11, the wall or central segment 12, and the distal segment 13. The elongated tubular structure 31/31A/31B/31C is inflated as discussed above by a fluid under pressure applied to the input port 131 or a differential pressure applied to the input/output ports 33/34/131/133. The input port 131 is often distal from the fenestrated balloon catheter 10 (e.g., outside of the patient while the fenestrated balloon catheter 10 is within the patient) and, is therefore contained within a bundle 25 that optionally contains any wires 41 or other conductors of power or sensor data (e.g., sensors 72/74 which are anticipated to be any sensors such as pressure sensors, cameras, etc.). In the embodiment shown, the wire(s) 41 are connected to an ultrasonic emitter 40.

The fenestrated balloon catheter 10 is typically guided through the body-tube 100 by a guide wire 105 that threads through an internal conduit 23 from the proximal end 21 to the distal end 22.

In embodiments that have proximal sensors 72 and distal sensors 74, it is anticipated that pressure and blood flow within the fenestrated balloon catheter 10 be measured to determine the insertion loss caused by the fenestrated balloon catheter 10, especially in embodiments such as shown in FIG. 3 in which it is anticipated that particulate material be captured within the fenestrated balloon catheter 10 (e.g., particulate material such as blood clots that are small enough to enter the fenestrated balloon catheter 10 through distal fenestrations 62 that are larger, yet particulate matter that is too large to pass through proximal fenestrations 60A that are smaller. Again, as stated above, for body fluid flow in the opposite direction, the proximal fenestrations 60A are larger than the distal fenestrations 60.

Fluid pressure is typically provided by pumps and monitored by sensors that are outside the patient connected to the fenestrated balloon catheter 10 input port 131/33. It is anticipated that the fluid pressure be adjusted to keep the fenestrated balloon catheter 10 inflated and, in cases of vascular dissections, to keep pressure against the body-tube 100 (e.g., blood vessel) at a level needed to control bleeding. In some embodiments, blood pressure and blood flow are measured by proximal sensors 72 and distal sensors 74.

Although any flow of a fluid 102 (e.g., blood, bile, urine, air) within the body-tube 100 is anticipated, in some usage scenarios, the fluid 102 flows as shown in FIGS. 1, 2, and 3, from the distal end of the fenestrated balloon catheter 10 towards the proximal end of the fenestrated balloon catheter 10.

The fenestrated balloon catheter 10 is shown inflated in FIGS. 2 and 3.

Referring to the embodiment of FIG. 2, in some embodiments, the distal fenestrations 62 and proximal fenestrations 60 are large enough for anticipated particulate matter (e.g., blood clot or debris) to enter into the fenestrated balloon catheter 10, pass through the fenestrated balloon catheter 10, and exit out of the proximal fenestrations 60 while allowing flow of a fluid (e.g., blood, urine, bile, air) through the body-tube 100 in which the fenestrated balloon catheter 10 is inserted. In some embodiments, the distal proximal fenestrations 62 are made to be smaller, thereby blocking any anticipated particulate matter (e.g., blood clot or debris) from entering into the fenestrated balloon catheter 10 while allowing flow of a fluid (e.g., blood, urine, bile, air) through the body-tube 100 in which the fenestrated balloon catheter 10 is inserted.

As shown in FIG. 3, in some embodiments, the distal fenestrations 62 are large enough for anticipated particulate matter (e.g., blood clot or debris) to enter into the fenestrated balloon catheter 10, but the proximal fenestrations 60A are smaller than the distal fenestrations 62, allowing flow of a fluid (e.g., blood, urine, bile, air) but capturing the particulate matter (e.g., blood clot or debris) that is smaller than the distal fenestrations 62, yet larger than the proximal fenestrations 60A. Such particulate matter is captured within the fenestrated balloon catheter 10.

Although it is anticipated that the fenestrations 60/60A/62 of the fenestrated balloon catheter 10 be of any shape (e.g., round, oval, triangular, rectangular), for brevity and clarity reasons, the fenestrations 60/60A/62 are shown as being round. When the fenestrations 62 at the distal end of the fenestrated balloon catheter 10 are round, the fenestrations 62 at the distal end of the fenestrated balloon catheter 10 have a first total area (e.g., sum of II r2 of each fenestration 62). When the fenestrations 60/60A at the proximal end of the fenestrated balloon catheter 10 are round, the fenestrations 60/60A at the proximal end of the fenestrated balloon catheter 10 have a second total area (e.g., sum of II r2 of each fenestration 60/60A).

As in some embodiments of the fenestrated balloon catheter 10, the proximal segment 11 and distal segment 13 are generally cone-shaped, the length (l) of each of the proximal segment 11 and distal segment 13 with respect to the radius (r) of each where the proximal segment 11 and distal segment 13 meet the wall 12 of the fenestrated balloon catheter 10 define an area of each of the proximal segment 11 and distal segment 13. Therefore, the surface area of each proximal segment 11 and distal segment 13 is approximately this II r1. In embodiments in which the length (l) is approximately twice the radius (r), to reduce or eliminate reduction of fluid flow through the fenestrated balloon catheter 10 after insertion and inflation, it is anticipated that the first area be a minimum of 50% of the surface area of the distal segment 13 and that the second area be a minimum of 50% of the surface area of the proximal segment 11. It is fully anticipated that the first area and second area be greater than 50% of the surface area of the respective segment 11/13 so long as the structure of the distal segment 13 and proximal segment 11 are maintained. (e.g., as the area of the fenestration 60/60A/62 approach the area of the respective proximal segment 11 and distal segment 13, then there is very little material devoted to the proximal segment 11 and distal segment 13, thereby reducing structural strength of each of the proximal segment 11 and distal segment 13. Therefore, if increased flow-thru is needed, the length (l) is increased to allow for greater fenestration 60/60A/62 area totals). It is also anticipated that the first area and/or the second area be less than 50% of the surface area of the respective segment 11/13, understanding that there will be some limitations to fluid flow through this embodiment of the fenestrated balloon catheter 10.

In some embodiments, the length (l) is four times the radius (r) and in such, to reduce or eliminate reduction of fluid flow through the fenestrated balloon catheter 10 after insertion and inflation, it is anticipated that the first area be a minimum of 25% of the surface area of the distal segment 13 and that the second area be a minimum of 25% of the surface area of the proximal segment 11. As above, it is fully anticipated that the first area and second area be greater than 25% of the surface area of the respective segment 11/13 so long as the structure of the distal segment 13 and proximal segment 11 are maintained. (e.g., as the area of the fenestration 60/60A/62 approach the area of the respective proximal segment 11 and distal segment 13, then there is very little material devoted to the proximal segment 11 and distal segment 13, thereby reducing structural strength of each of the proximal segment 11 and distal segment 13). Therefore, if increased flow-thru is needed, the length (l) is increased to allow for greater fenestration 60/60A/62 area totals. It is also anticipated that the first area and/or the second area be less than 25% of the surface area of the respective segment 11/13, understanding that there will be some limitations to fluid flow through this embodiment of the fenestrated balloon catheter 10.

Equivalent elements can be substituted for the ones set forth above such that they perform in substantially the same manner in substantially the same way for achieving substantially the same result.

It is believed that the system and method as described and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely exemplary and explanatory embodiment thereof. It is the intention of the following claims to encompass and include such changes.

The invention claimed is:

1. A fenestrated balloon catheter comprising:

a body having a proximal segment, a central segment, and a distal segment, the proximal segment having a first set of fenestrations and the distal segment having a second set of fenestrations, the body made of a resilient material;

a central lumen configured to pass a guidewire there through, the central lumen interfaced between the proximal segment and the distal segment;

an elongated tubular structure is affixed to an inside surface of the proximal segment, the central segment, and the distal segment, the elongated tubular structure configured to bypass the first set of fenestrations and the second set of fenestrations; and whereas when the elongated tubular structure is pressurized, the body is configured to expand and when the elongated tubular structure is depressurized, the body is configured to contract.

2. The fenestrated balloon catheter of claim 1, wherein the elongated tubular structure is wound around a first inside surface being of the proximal segment, a second inside surface being of the central segment, and a third inside surface being of the distal segment.

3. The fenestrated balloon catheter of claim 1, wherein a first section of the elongated tubular structure is wound around a first outside surface being of the proximal segment, a second outside surface being of the central segment, and a third outside surface being of the distal segment and a second section of the elongated tubular structure is wound around a first inside surface being of the proximal segment, a second inside surface being of the central segment, and a third inside surface being of the distal segment.

4. The fenestrated balloon catheter of claim 1, wherein the elongated tubular structure is bifurcated having an input port interfaced to a first side of the elongated tubular structure at a proximal end of the elongated tubular structure and an output port interfaced to a second side of the elongated tubular structure at the proximal end of the elongated tubular structure and a connection between the first side and the second side at a distal end of the elongated tubular structure.

5. The fenestrated balloon catheter of claim 1, wherein the proximal segment and the distal segment are conically shaped and the central segment is tubularly shaped.

6. The fenestrated balloon catheter of claim 1, wherein the first set of fenestrations have a larger cross-sectional area than a smaller cross-sectional area of the second set of fenestrations such that particulate material having a cross-sectional size of between the larger cross-sectional area and the smaller cross-sectional area is able to enter the fenestrated balloon catheter through the first set of fenestrations and are not able to exit the fenestrated balloon catheter through the second set of fenestrations.

7. The fenestrated balloon catheter of claim 1, further comprising:

a sensor interfaced to the proximal segment or the distal segment.

8. The fenestrated balloon catheter of claim 1, further comprising:

an ultrasonic emitter device affixed to the central segment.

9. A system for delivering therapy within a body-tube, the system comprising:

a fenestrated balloon catheter that includes a body having a proximal segment, a central segment, and a distal segment, the proximal segment having a first set of fenestrations and the distal segment having a second set of fenestrations, the body made of a resilient material; an elongated tubular structure is affixed to an inside surface of the proximal segment, the central segment, and the distal segment; and the fenestrated balloon catheter includes an internal conduit for accepting a guide wire;

the guide wire being configured to be positioned in the body-tube;

an end of the guide wire is threaded through the internal conduit of the fenestrated balloon catheter such that the fenestrated balloon catheter is configured to be guided into the body-tube by the guide wire;

the fenestrated balloon catheter is pushed through the body-tube until the fenestrated balloon catheter reaches a location for delivering the therapy; and fluid pressure is injected into the elongated tubular structure, responsive to the fluid pressure, the fenestrated balloon catheter is configured to expand within the body-tube such that the fenestrated balloon catheter either touches inner walls of the body-tube or expands to stretch the body-tube.

10. The system of claim 9, wherein the body-tube is a blood vessel.

11. The system of claim 10, wherein when the fluid pressure is injected into the elongated tubular structure and the fenestrated balloon catheter expands, blood flowing within the blood vessel passes into the first set of fenestrations, through the central segment, and out of the second set of fenestrations.

12. The system of claim 10, wherein the first set of fenestrations have a larger cross-sectional area than a smaller cross-sectional area of the second set of fenestrations such that a blood clot having a cross-sectional size of between the larger cross-sectional area and the smaller cross-sectional area is able to enter the fenestrated balloon catheter through the first set of fenestrations and is not able to exit the fenestrated balloon catheter through the second set of fenestrations, thereby retaining the blood clot within the fenestrated balloon catheter.

13. A method for delivering therapy within a body-tube, the method comprising:

positioning a guide wire in the body-tube;

threading an end of the guide wire through an internal conduit of a fenestrated balloon catheter, the fenestrated balloon catheter having a body made of a resilient material and having a proximal segment, a central segment, and a distal segment, the proximal segment having a first set of fenestrations and the distal segment having a second set of fenestrations; an elongated tubular structure is affixed to an inside surface of the proximal segment, the central segment, and the distal segment;

pushing the fenestrated balloon catheter through the body-tube until the fenestrated balloon catheter reaches a location for delivering the therapy; and providing fluid pressure into the elongated tubular structure, thereby expanding the fenestrated balloon catheter within the body-tube such that the elongated tubular structure applies an outward force against the inside surface of at least the central segment to expand the central segment.

14. The method of claim 13, wherein the body-tube is a blood vessel.

15. The method of claim 14, wherein after providing the fluid pressure into the elongated tubular structure, the central segment expanding and blood flowing within the blood vessel passes into the first set of fenestrations, through the central segment, and out of the second set of fenestrations.

16. The method of claim 14, wherein the first set of fenestrations have a larger cross-sectional area than a smaller cross-sectional area of the second set of fenestrations such that a blood clot having a cross-sectional size of between the larger cross-sectional area and the smaller cross-sectional area entering the fenestrated balloon catheter is not able to exit the fenestrated balloon catheter through the second set of fenestrations, thereby retaining the blood clot within the fenestrated balloon catheter.

* * * * *